US005651828A

United States Patent [19]
Whistler

[11] Patent Number: 5,651,828
[45] Date of Patent: Jul. 29, 1997

[54] FAT SUBSTITUTE FOR PROCESSED FOODS

[75] Inventor: Roy L. Whistler, West Lafayette, Ind.

[73] Assignee: Lafayette Applied Chemistry, Inc., West Lafayette, Ind.

[21] Appl. No.: 315,332

[22] Filed: Sep. 30, 1994

[51] Int. Cl.$^6$ .............. C08B 30/12; A23L 1/10; C12P 19/20
[52] U.S. Cl. .............. 127/32; 127/29; 127/36; 127/69; 426/28; 426/531; 435/96
[58] Field of Search ............... 127/29, 32, 36, 127/38, 69, 70, 71; 435/96; 426/28, 531

[56] References Cited

U.S. PATENT DOCUMENTS

| | | | |
|---|---|---|---|
| 3,023,104 | 2/1962 | Battista | 426/549 |
| 3,351,489 | 11/1967 | Battista | 127/32 |
| 3,666,557 | 5/1972 | Jensen et al. | 127/32 |
| 3,876,629 | 4/1975 | Lotzgesell | 260/233.3 R |
| 3,922,197 | 11/1975 | Leach et al. | 435/96 |
| 3,922,198 | 11/1975 | Kuske et al. | 127/32 |
| 3,962,465 | 6/1976 | Richter et al. | 435/96 |
| 3,986,890 | 10/1976 | Richter et al. | 426/48 |
| 4,072,535 | 2/1978 | Short et al. | 127/28 |
| 4,308,294 | 12/1981 | Rispoli et al. | 426/564 |
| 4,393,202 | 7/1983 | Breuninger | 536/102 |
| 4,492,714 | 1/1985 | Cooper et al. | 426/602 |
| 4,510,166 | 4/1985 | Lenchin et al. | 426/565 |
| 4,551,177 | 11/1985 | Trubiano et al. | 106/210 |
| 4,585,858 | 4/1986 | Molotsky | 536/41 |
| 4,615,892 | 10/1986 | Morehouse et al. | 426/250 |
| 4,782,143 | 11/1988 | Morehouse et al. | 536/102 |
| 4,911,946 | 3/1990 | Singer et al. | 426/658 |
| 4,917,915 | 4/1990 | Cain et al. | 426/573 |
| 4,985,082 | 1/1991 | Whistler | 426/661 |
| 5,051,271 | 9/1991 | Iyengar et al. | 426/658 |
| 5,275,837 | 1/1994 | Eastman | 426/661 |

FOREIGN PATENT DOCUMENTS

| | | | |
|---|---|---|---|
| 770089 | 3/1957 | United Kingdom | 536/102 |
| PCT/NL83/00007 | 2/1983 | WIPO | C13L 1/08 |
| PCT/US91/01029 | 9/1991 | WIPO | A23G 3/00 |

OTHER PUBLICATIONS

"Scanning Electron Microscopy of Enzyme Digested Digested Varagu Starch Granules", Paramahans, S.V. and Tharanathan, R.N., Starch/Starke, No. 34, pp. 73–76 (1982) month not available.

"Degradation of Starch Granules by Alpha–Amylase of Streptomyces precox NA–273", Takaya, T., Sugimoto, Y., Wako, K. and Fuwa, H., Starch/Starke, 31 No. 6, pp. 205–209 (1979) month not available.

"Scanning Electron–Microscopy of Starch Granules With or Without Amylase Attack", Fuwa, H., Sugimoto, Y., and Takaya, T. (1978) May 1978.

"New Starches. V. Properties of the Small Starch Granules from Amaranthus retroflexus", P.V. Subba Rao and K.J. Goerhing, Cereal Chemistry, vol. 47, No. 5 (1970) month N/A.

"Experience on Isolation, Properties and Cross–linkage of Fine Granule Starches", E. Wilhelm, Institute for Starch and Potato Technology, Schutzenbert, 12, D–4930, Detmold, Germany, Cereal Foods World, vol. 35, No. 8. (1990) month N/A.

"Characterization of Starch Granules from Waxy, Nonwaxy, and Hybrid Seeds of Amaranthus Hypochondriacus L." Y. Konishi, Agric. Biol. Chem., 49 (7), 1965–1971, 1985 month N/A.

"Susceptibility of Various Starch Granules to Amylases as Seen by Scanning Electron Microscope", Fuwa, H., Sugimoto, Y., Tanaka, M., Glover, D.V. Staerke 30(6), pp. 186–191 (1978) (Abstract) month not available.

"Degradation of Various Starch Granules by Glucoamylases of Rhizopus Amagasakiens, Rhizopus Niveus, and Endomyces", Takaya, T., Glover, D.V., Sugimoto, Y., Tanaka, M., Fuwa, H., Denpun Kagaku 29(4), pp. 287–293 (1982) (Abstract) month not available.

"Hydrolysis of Large and Small Starch Granules From Normal and Waxy Barley Cultivars by a–Amylases From Barley Malt", MacGregor, A.W., Ballance D.L., Cereal Chem., pp. 397–402 57(6) (1980) (Abstract) month not available.

"Amyloglucosidase–catalysed Erosion of Native, Surface–modified and Chlorine–treated Wheat Starch Granules. The Influence of Surface Protein", Greemwell, P., Evers, A.D. Gough, B.M., and Rusell, P.L., Journal of Cereal Science, 3, pp. 279–293 Apr. (1985) (abstract).

Colloidal Macromoleclar Phenomena, Part II, Novel Microcrystals of Polymers, Journal of Applied Polymer Science, vol. 11, pp. 481–498 (1967) month not available.

Colloids:Particle Gels, by Eric Dickinson, Chemistry & Industry, pp. 595–599 (Oct. 1990).

Paselli SA2 AVEBE Product Information Ref No. 05.12.31.167 EF, AVEBE b. a. Internation Marketing and Sales, Foxhof, Holland, (Jun. 1988).

"Preparation and Properties of Small–Particle Corn Starch", J.Jane, L. Shen, L. Wang and C.C. Maningat, Cereal Chemistry, 69 No. 3 pp. 280–283 (1992) month not available.

"Stucture versus Functional Relationships of a New Starch–Based Fat Replacer", Starch/Starke, 45 No. 7 pp. 221–226 (1993) month not available.

"The Effects of Enzyme Hydrolysis on the Properties of Potato, Cassava, and Amaranth Starches." Gorenstein, Shela, and Lii, Cheng-yi Starch/Stärke 44 (1992), pp. 461–466.

Primary Examiner—Glenn Caldarola
Assistant Examiner—Patricia L. Hailey
Attorney, Agent, or Firm—Barnes & Thornburg

[57] ABSTRACT

Small granule starches are subjected to partial hydrolysis with alpha-amylase or glucoamylase to produce a novel granular starch composition having an enzymatically hydrolyzed surface appearing diffuse and substantially non-porous under microscopic examination and exhibiting crystallinity characteristic of the corresponding native starch granules. The partially hydrolyzed granular starch exhibits fat mimic characteristics for use in reduced calorie processed foods.

13 Claims, No Drawings

FAT SUBSTITUTE FOR PROCESSED FOODS

FIELD OF THE INVENTION

This invention relates to a modified starch composition. More particularly, the present invention is directed to a partially hydrolyzed small granular starch useful as a fat substitute in processed, reduced-calorie foods.

BACKGROUND AND SUMMARY OF THE INVENTION

The food industry has invested a significant research and development effort to identify food ingredient products that can exhibit a sensory perception of fattiness in foods without the high calorie content of common oil and fat-containing ingredients. Generally, it has been found that the fatty sensation detected in the mouth is entirely a phenomenon of rheology. There are no sensors in the mouth for fats as there are for sweetness and saltiness. Instead, the sensation of fattiness is a complex sensation involving interrelated viscosity and flowability properties of a food product.

The scientific literature contains multiple references to the organoleptic sensation produced in the mouth By particular components of foods. For example, certain protein and carbohydrate compositions are proposed as fat replacements in U.S. Pat. No. 4,911,946 and references identified therein. Carbohydrates and proteins have less than one-half of the calories of available metabolic energy than carbohydrates on a per gram basis. Two significant proteins, namely whey protein and egg white protein, in the form of microspheres of about 1–10 microns have been made by at least two companies for use as fat mimics. U.S. Pat. No. 4,911,946 also suggests that small, substantially spherical carbohydrate-based particles, including small whole starch granules in the 0.1–3 micron diameter range, are acceptable fat mimics.

This invention relates to an improved granular starch-derived composition for use as a fat mimic. It is based on the discovery that small granule starches, generally those having an average granule size of 5 microns or less, more particularly those averaging 3 microns or less in diameter undergo an unusual, heretofore unrecognized, surface modification, upon partial hydrolysis with amylase at temperatures below the starch gelatinization temperature. Generally, it is reported in the patent and non-patent literature that enzymatic hydrolysis of granular starch at temperatures below the starch gelatinization temperature provides porositized or cavitated granule surfaces readily discernible by microscopic examination. In many instances the starch granules are reduced to a sponge-like structure deriving from uneven hydrolysis. In theory the starch polymers in the regions of lesser crystallinity undergo enzyme mediated hydrolysis at higher rates than those areas of greater crystallinity on the starch surface.

It has been found that granular starches having an average granule diameter of about 5 microns or less, for example amaranth, quinoa, and taro are not porositized or cavitated upon treatment with amylase at temperatures below the respective granular starch gelatinization temperatures. Instead, enzymatic hydrolysis of such granular starches under nongelatinizing conditions produce partially hydrolyzed granules which have a surface appearing very diffuse or amorphous and substantially non-porous under microscopic examination, and which exhibit crystallinity characteristic of the corresponding native starch granules, as determined by x-ray or microscopic analysis with polarized light.

The partially hydrolyzed small granule starch compositions in accordance with this invention exhibit improved fat substitute functionality. When used as a substitute for at least a portion of the fat content of processed foods, the hydrolyzed small granule starch imparts the sensory perception of fattiness with less calorie content and without compromise of other organoleptic qualities of the modified food product. The enzyme hydrolyzed small granule starches in accordance with the invention are optionally treated with a surface modifying agent to complement the functional qualities of the starch composition.

Thus, in accordance with the present invention there is provided a partially hydrolyzed small granule starch which exhibits exceptional fat mimic characteristics in processed foods.

Another embodiment of the present invention provides a method of preparing an improved granular starch based fat substitute for processed foods.

Still another embodiment of the present invention is a process for modifying the recipe of a processed food to reduce the calorie content without compromising its organoleptic qualities.

DETAILED DESCRIPTION OF THE INVENTION

Granular starches useful for preparation of the fat mimics in accordance with this invention are those having an average particle size of 5 microns or less, more preferably about 3 microns or less. Suitable sources of such granular starches include amaranth, quinoa and taro. Most preferred sources of the small granular starch used in accordance with this invention are amaranth and quinoa, each of which have an average starch granule size of about 1 micron. Amaranth starch is most preferred. Its seeds are readily processed into flour which can be washed with dilute (0.25%) sodium hydroxide solution to provide a good quality starch product with very low fat and protein content.

The techniques for enzyme hydrolysis of granular starch are generally well known in the art. Conditions for partial hydrolysis of granular starch at temperatures below the starch gelatinization temperature is described for example in U.S. Pat. Nos. 4,985,082 and 4,551,177, the disclosures of which are expressly incorporated herein by reference.

In accordance with this invention, there is provided a method of preparing an improved granular-starch-based fat substitute for processed foods. The method comprises the steps of hydrolyzing a small granule starch with an amylase, for example an alpha-amylase and/or a glucoamylase in an aqueous medium for a period of time sufficient to solubilize at least about 5% by weight of the starch, and thereafter recovering the partially hydrolyzed granular starch from the aqueous hydrolysis medium. Any of a wide variety of art recognized alpha-amylases or glucoamylases including those derived from fungal, bacterial or animal origin can be utilized. Typically the enzyme mediated, partial hydrolysis of the granular starch base is carried out using moderately high amounts of enzyme, for example about 0.1 to about 1% by weight, at a temperature below the starch's gelatinization temperature, for example, about 30° C. to about 60° C. for a period of time sufficient to solubilize about 5 to about 40% by weight of the starch, typically for a time ranging from about 5 minutes to about 2 hours. Longer reaction times can be used but such results in lower product yields without added functionality. The rate of hydrolysis of the granular starch in the starch slurry reaction medium is generally directly proportional to the enzyme concentration and the temperature of the reaction medium so long as the temperature does not exceed the gelatinization temperature of the starch nor the denaturization temperature of the enzyme. The rate of reaction is also pH dependent and optimum pH is dictated by the nature of alpha-amylase or glucoamylase or enzyme combination utilized in the granular starch hydrolysis reaction mixture.

The enzyme treated granular starch is recovered from the aqueous hydrolysis medium by filtration or centrifugation and dried. Microscopic examination of the partially hydrolyzed granular starch thereby produced shows it to have a substantially non-porous, diffuse, almost "fuzzy" appearing surface, but it still exhibits crystallinity characteristic of the corresponding native starch granules as determined by x-ray or microscopic analysis under polarized light.

Thus, in accordance with this invention an aqueous slurry of amaranth starch is treated at 37° with commercially available glucoamylase or alpha-amylase for a period of time sufficient to solubilize about 5 to about 40 weight percent, more typically about 5 to about 20 weight percent of the starch. Thereafter the reaction slurry is centrifuged and the starch product is washed with ethanol and dried to recover the partially hydrolyzed granular starch. The weight of recovered enzyme-treated starch decreases with increased reaction time. A reaction time of about 3 to about 5 minutes resulted in recovery of an amount of partially hydrolyzed amaranth starch equal to about 93% of the weight of the granular starch starting material. Hydrolysis times under similar conditions for 15 minutes, 30 minutes, 1 hour and 2 hours provided hydrolyzed granular starch yields of 92%, 90%, 83% and 60%, respectively. The partially hydrolyzed amaranth granules produced after a hydrolysis time of 15 minutes at 37° C. are about 0.6 microns in diameter compared with the untreated granules of about 1 micron in diameter. The product shows birefringence when placed under a microscope and viewed with polarized light establishing that at least the inner portions of the granules have retained their native crystalline form. Such is verified by x-ray analysis.

Optionally, the partially hydrolyzed small granule starches in accordance with this invention can be chemically modified to optimize the functional characteristics associated with its use as a fat substitute for processed foods. Chemical treatments which work to increase the lipophilic character of the starch composition are particularly useful. Chemical modification of the starch composition can be effected either by adsorption of surface modifying agents or by reaction of the starch with starch reactive chemical reagents which form covalent bonds with the starch. Such starch modifying agents include chemical cross-linking agents which can be employed to enhance the gelatinization temperature of the enzyme modified small granule starches. Any of the wide variety of food acceptable starch modifying agents can be employed, including more particularly those described in U.S. Pat. No. 4,985,082, incorporated herein by reference. The optional chemical modification of the partially hydrolyzed small granular starch composition in accordance with this invention is preferably performed after enzyme treatment; however, chemical modification prior to enzyme treatment is still within the scope of this invention as is subjecting the granular starch to treatment with two or more chemical modifying agents at the same time or at different points in the process of its manufacture.

The partially hydrolyzed small granular starch in accordance with this invention finds use as a food ingredient and a substitute for at least a portion of the fat content in processed foods to provide low calorie form of the food product with minimal compromise of organoleptic quality. Thus in accordance with another embodiment of the present invention, there is provided a process for modifying the recipe of a processed food containing a fat ingredient to reduce the calorie content of the processed food. The method comprises the step of substituting a first portion of the partially hydrolyzed small granule starch of this invention for a second portion of the fat in the processed food. The weight ratios of the first and second portions of starch and replaced fat, respectively, can range from about 2 to 1 to about 1 to 10. The partially hydrolyzed small granule starch mimics the mouth feel of fats in processed foods. Thus the present starch composition can be substituted for at least a portion of the fat, for example, in spoonable dressings and frozen dessert compositions in accordance with this invention. Thus, partially hydrolyzed amaranth starch can be used to replace at least a portion of the heavy cream component of an ice cream formulation comprising sugar, non-fat milk solids, corn syrup, stabilizer, heavy cream, skim milk, vanilla, and water. The percent fat reduction is varied from 15 to 75% by adding about 2% by weight of hydrolyzed amaranth starch in accordance with this invention and replacing correspondingly increasing amounts of the heavy cream ingredient with skim milk.

The diffuse surface structure of the amylase treated small granule starches in accordance with this invention appears somewhat like that of microcrystalline cellulose (Avicel), a product commercially produced by acid hydrolysis of cellulose. That product is recognized as a food grade cellulose and is generally insoluble, but readily dispersible in water. It finds numerous uses in the food industry. It is contemplated therefore that the partially hydrolyzed small granular starch in accordance with this invention will find use in the food industry comparable to those uses recognized for microcrystalline cellulose.

Although the invention has been described in detail with reference to its preferred embodiments, variations and modifications exist within the scope and spirit of the invention as defined in the following claims.

I claim:

1. A method for preparing an improved granular-starch based fat substitute for processed foods, said method comprising the step of hydrolysing a small granule starch having an average diameter less than about 5 microns with an amylase in an aqueous medium at a temperature below the gelatinization temperature of the small granule starch for a period of time sufficient to solubilize at least about 5% by weight of the starch, and recovering the partially hydrolyzed granular starch from the aqueous medium.

2. The method of claim 1 wherein the amylase comprises alpha-amylase or glucoamylase.

3. The method of claim 1 wherein the enzymatic hydrolysis is carried out for a period of time sufficient to solubilize about 5 to about 20% by weight of the starch.

4. The method of claim 1 wherein the amylase is a glucoamylase.

5. The method of claim 1 wherein the amylase is an alpha-amylase.

6. The method of claim 1 wherein the small granular starch is amaranth or quinoa starch.

7. A granular starch composition comprising surface hydrolyzed granules of starch selected from the group consisting of amaranth, quinoa, and taro, said granules having an average diameter less than about 5 microns and said granules having been hydrolyzed with an amylase in an aqueous medium at a temperature below the gelatinization temperature of the starch granules to provide starch granules having an enzymatically hydrolyzed surface appearing substantially non-porous and diffuse under microscopic examination and exhibiting crystallinity characteristic of the corresponding native starch granules as determined by x-ray or microscopic analysis with polarized light.

8. The granular starch composition of claim 7 wherein the starch is amaranth starch.

9. The granular starch composition of claim 7 wherein the starch is quinoa starch.

10. A granular starch composition comprising surface hydrolyzed granules of starch, said granules having an average diameter less than 5 microns, said granules having been hydrolyzed with an amylase in an aqueous medium at a temperature below the gelatinization temperature of the starch for a period of time sufficient to solubilize at least about 5% by weight of the starch, said granules having an enzymatically hydrolyzed surface appearing substantially non-porous under microscopic examination and exhibiting crystallinity characteristic of the corresponding native starch granules as determined by x-ray or microscopic analysis with polarized light.

11. The starch composition of claim 10 wherein the starch is amaranth starch.

12. The granular starch composition of claim 10 wherein the starch is quinoa starch.

13. The granular starch composition of claim 10 wherein the starch is taro starch.

* * * * *